| United States Patent [19] | [11] Patent Number: 4,945,174 |
| --- | --- |
| Huser et al. | [45] Date of Patent: Jul. 31, 1990 |

[54] PALLADIUM-BASED COMPLEXES

[75] Inventors: Marc Huser; John Osborn, both of Strasbourg, France

[73] Assignee: Rhone Poulenc Chimie, Courbevoie, France

[21] Appl. No.: 383,077

[22] Filed: Jul. 20, 1989

[30] Foreign Application Priority Data

Jul. 20, 1988 [FR] France .................................. 88 09789

[51] Int. Cl.$^5$ ............................................... C07F 15/00
[52] U.S. Cl. ......................................... 556/16; 556/21; 556/22; 556/23
[58] Field of Search .................... 556/16, 21, 23, 22

[56] References Cited

U.S. PATENT DOCUMENTS

| | | | |
| --- | --- | --- | --- |
| 3,954,821 | 5/1976 | Herskovitz et al. | 556/16 |
| 4,098,807 | 7/1978 | Stone et al. | 556/23 X |
| 4,119,652 | 10/1978 | Knowles et al. | 556/23 |
| 4,196,135 | 4/1980 | Ewomoto et al. | 556/23 X |
| 4,229,605 | 10/1980 | Kozaki | 556/23 X |
| 4,229,606 | 10/1980 | Kozaki | 556/23 X |
| 4,491,546 | 1/1985 | Hawes | 556/23 X |

*Primary Examiner*—Paul F. Shaver
*Attorney, Agent, or Firm*—Finnegan, Henderson, Farabow, Garrett and Dunner

[57] ABSTRACT

New palladium-based complexes permit the complexing of chlorinated aromatic derivatives. These complexes make it possible to perform hydrogenolysis, hydrocarbonylation and alkoxycarbonylation reaction on chlorinated compounds.

15 Claims, No Drawings

PALLADIUM-BASED COMPLEXES

FIELD OF THE INVENTION

The present invention relates to new complexes, and more particularly to new palladium-based complexes. The present invention relates more particularly to the formation of complexes of palladium and of chlorinated aromatic compounds.

BACKGROUND OF THE INVENTION

Complexes of palladium and of triphenylphosphine have been known for a very long time. For example, the preparation and the use of complexes based on palladium and triphenylphosphine are described by Heck in U.S. Pat. Nos. 3,960,932 and 3,988,358. These complexes permit carbonylation reactions of aromatic bromo or iodo compounds, but do not permit in any circumstance the carbonylation of chlorinated aromatic compounds.

When one skilled in the art, reading the prior art, attempted to carbonylate aromatic compounds in a homogeneous medium, it was always necessary to start with aromatic bromo or iodo compounds and then to complex them with a complex palladium salt. It has also been known for a very long time that brominated aromatic compounds are much more costly in price than chlorinated compounds. The problem of carbonylation of chlorinated aromatic compounds is a problem which the present invention has attempted to solve.

DESCRIPTION OF THE INVENTION

The new complexes of the present invention correspond to the following formula (I):

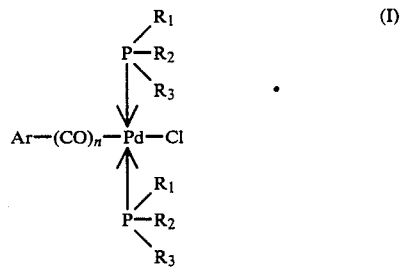
(I)

in which

Ar is a substituted mono- or polycyclic or heterocyclic aromatic radical, each of $R_1$, $R_2$, and $R_3$ is an identical or different group selected from cyclohexyl, benzyl and isopropyl radicals, it being possible for one of groups $R_1$, $R_2$, and $R_3$ to be replaced by a phenyl group when the other two are cyclohexyl groups, and n is an integer equal to 0 or 1.

The complexes of formula (I) of the present invention are prepared by at least three methods of preparation.

According to a first method of preparation, a compound of the following formula (II):

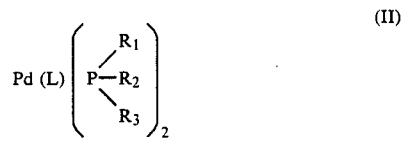
(II)

in which the moiety L is a group which is labile in the presence of ArCl, and the groups $R_1$, $R_2$, and $R_3$ have the same meaning as in formula (I), is brought into contact with an aromatic halo compound of the formula ArCl and optionally with carbon monoxide when n is other than 0.

According to a second method of preparation of complexes of formula (I), 1. a complex of palladium in the zero oxidation state selected from either:

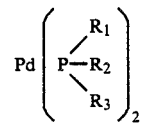

or $Pd(L)_3$ in the presence of at least two equivalents of phosphine corresponding to the formula

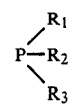

is brought into contact with 2. the chloroaromatic compound of the formula ArCl and, optionally carbon monoxide when n is other than zero.

According to a third method of preparation of the complexes of formula (I), a salt of palladium in the oxidation state II selected for example, from palladium dichloride, dibromide or diiodide, palladium diacetate, palladium nitrate, palladium sulfate and palladium oxide, is brought into contact with the chloroaromatic compound and at least two equivalents of a phosphine of formula

in the presence of a reducing agent consisting of hydrogen and optionally in the presence of carbon monoxide when n is other than zero.

Within the scope of the present invention, a labile group (L) means any group which can be easily exchangeable in the presence of ArCl.

Among these groups there may be mentioned, no limitation being implied:
dibenzylideneacetone (DBA)
alkylene, and preferably ethylene, groups.

In all the above-mentioned preparative procedures, it is preferred to operate in an organic solvent selected from
aromatic solvents such as benzene, toluene and xylenes
aliphatic solvents
ethers such as diisopropyl ether
amides such as dimethylformamide
nitriles such as benzonitrile.

The chlorinated aromatic compound can also be used as a reaction medium.

As stated above, when starting with a palladium complex which does not contain any phosphine, it is preferred to use at least 2 moles of phosphine per atom of palladium and more preferably from 2 to 5 moles.

It is preferred to employ a quantity of solvent such as to make the concentration of palladium complex or salt in the medium from 1 to 100 mmols per liter.

The temperature at which the reactants are brought into contact is preferably from ambient temperature to 200° C. The duration of contact will vary with the temperature, but a duration of from one hour to approximately a day appears to be preferred.

When n is other than zero, that is, when the complex of formula (I) contains at least one —CO— group, the preparation of this compound is carried out in the presence of carbon monoxide. The pressure of carbon monoxide of from 1 to 50 bars is preferred.

The complex of formula II, used as a starting material for the synthesis of the complex of formula I in which L is dibenzylideneacetone (DBA), is a new product which is claimed as such. It corresponds to the following formula III:

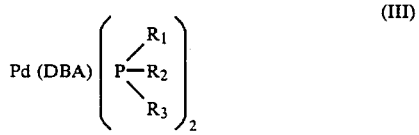   (III)

in which $R_1$, $R_2$, and $R_3$ have the same meaning as above.

It is used for the preparation of the complex of formula I. It is prepared by bringing dibenzylidene acetone - palladium, a complex salt, into contact with at least 2 equivalents of a phosphine of the formula

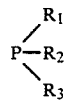

in an organic solvent.

The organic solvent is the same as that which can be used for the synthesis of the complexes of formula I.

The complexes of formula I which are obtained within the scope of the present invention are employed especially in hydrogenolysis, hydrocarbonylation or alkoxycarbonylation reactions, such as described in patent applications filed concurrently with the present application.

The application will be described more completely with the aid of the following examples which must not in any event be considered as limiting the invention.

In the following examples, the abbreviations employed have the following meanings:
DBA = dibenzylideneacetone
Cy = cyclohexyl
Bz = benzyl
Ph = phenyl

EXAMPLE 1

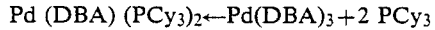

500 mg (0.55 mM) of Pd(DBA)$_3$ and 458 mg (1.65 mM, that is a 50% excess) of PCy$_3$ were dissolved in 50 ml of benzene. The solution of the mixture was heated to 50° C. for 16 hours and the metallic palladium formed was then separated off by filtration; after the filtrate had been evaporated to dryness, the orange-colored solid thus obtained was washed with 40 ml of ether to extract the excess DBA and phosphine. A yellow powder (342 mg, Y=70%) was isolated and characterized by NMR ($^1$H and $^{31}$P and IR).

IR (nujol) ($\nu$ cm$^{-1}$): 1640 (C=O); 1575 and 1585 (C=C). $^1$H NMR(200 MHz, C$_6$D$_6$) $\delta$ (ppm): 1.3 to 2.3 (m, 66H, aliphatic protons of PCy$_3$); 7.1 to 7.7 (m, 10H, aromatic H of DBA); 5.1 (m, 2H, olefinic protons); 8.2 (m, 2H, olefinic protons). $^{31}$P-[$^1$H]NMR (80 MHz, C$_6$D$_5$CD$_3$) $\delta$: 35 ppm.

EXAMPLE 2

1.3 g (1.44 mM) OF PD(DBA)(PCy$_3$)$_2$ were dissolved in 100 ml of chlorobenzene. The solution was kept stirred at 60° C. for 2 hours and was then filtered to remove the traces of metallic palladium. After the filtrate had been evaporated down, the solid thus obtained was washed with 50 ml of ether to extract the DBA released during the reaction. 850 mg (1.09 mM, Y=76%) of a white product were isolated.

IR(nujol) $\nu$ (cm$^{-1}$): 705 and 740 (monosubstituted aromatic C—C).

$^1$H NMR(200 MHz, C$_6$D$_6$) $\delta$ (ppm): 7.74 (d, 1H, ortho aromatic hydrogen); 7.13 (t, 2H, meta aromatic hydrogens; 7.00 (t, 2H, para aromatic hydrogens); 1.2 to 2.35 (m, 66H, aliphatic protons of PCy$_3$).

$^{31}$P-[$^1$H]NMR (80 MHz, C$_6$D$_6$) $\delta$ (ppm): 22.9 (s).

EXAMPLE 3

Carbonylation of the Pd(PCy$_3$)$_2$(C$_6$H$_5$)Cl complex

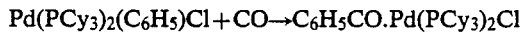

150 mg (0.2 mM) of Pd(PCy$_3$)2(C$_6$H$_5$)Cl were dissolved in 15 ml of benzene and were placed in an autoclave under 30 bars of CO. The colorless solution stirred at ambient temperature quickly turned yellow, but reaction was complete only after 20 hours. After filtration and evaporation of the filtrate, a yellow product (120 mg, Y=75%) was isolated.

IR(nujol) $\nu$ (cm$^{-1}$) 1630 (C=O).

$^1$H NMR (200 MHz,m C$_6$D$_6$) $\delta$ (ppm): 7.47, 7.95 and 9.60 (broad peaks, 5H, aromatic protons); 1.05 to 2.60 (m, 66H, aliphatic protons of PCy$_3$).

$^{31}$P-[$^1$H]NMR (80 MHz, C$_6$D$_6$) $\delta$ (ppm): 22.4 (s).

EXAMPLE 4

Synthesis of the Pd(PCy$_3$)$_2$(C$_6$H$_5$)Cl complex in one stage from Pd(DBA)$_3$ A solution containing 13.8 g (17 mmol) of Pd(DBA)$_3$ and 10.5 g (37.5 mmol, that is a 10% excess) of tricyclohexylphosphine in 400 ml of freshly distilled and degassed chlorobenzene was stirred for 2 hours at ambient temperature and was then heated to 55° C. for 16 hours. The dark-yellow solution thus obtained was filtered slowly to remove the traces of metallic palladium and was then evaporated to dryness. The yellow solid was washed with 200 m of ether to dissolve the DBA released during the reaction and the excess phosphine, and then with 20 ml of THF to remove the traces of unconsumed Pd(DBA)$_3$, and finally with 100 ml of ether. The white product (10.8 g, 13.9 mmol, Y=82%) was dried under vacuum and analyzed by IR, $^1$H and $^{31}$P NMR.

IR(nujol) $\nu$ (cm$^{-1}$): 705 and 740 (monosubstituted aromatic C—C). $^1$H NMR (200 MHz, C$_6$D$_6$) $\delta$ (ppm) : 7.74 (d, 1H, ortho aromatic hydrogen); 7.13 (t, 2H, meta aromatic hydrogens); 7.00 (t, 2H, para aromatic hydrogens); 1.2 to 2.35 (m, 66H, aliphatic protons of PCy3).
$^{31}$P-[$^1$H]NMR (80 MHz, C$_6$D$_6$) δ (ppm): 22.9 (s).

EXAMPLE 5

Pd(DBA)(PPhCy$_2$)$_2$←Pd(DBA)$_3$ + 2PPhCy$_2$

A solution containing 970 mg (3.53 mmol) of PCy$_2$Ph and 1.27 g (1.57 mmol) of Pd(DBA)$_3$ in 50 ml of toluene was stirred for 3 hours at ambient temperature. After evaporation of the solvent, the orange-colored solid was washed with ether to dissolve the DBA released during the reaction and the slight excess of phosphine; 950 mg (1.07 mmol, Y - 84%) of an air sensitive orange-colored product was isolated.

IR(nujol) ν (cm$^{-1}$): 1640 (C═O). $^1$H NMR (200 MHz, C$_6$D$_6$) δ (ppm): 0.5–2.7 (m, 44H, Cy); 5.35 (m, 2H, olefinic H); 8.1 (m, 2H, olefinic H); 6.9–7.7 (m, 20H, aromatic H). $^{31}$P-[$^1$H]NMR (80 MHz, C$_6$D$_6$) δ (ppm): 31.7 (broad s).

EXAMPLE 6

Pd(DBA) (PBz$_3$)$_2$←Pd(DBA)$_3$ + 2 PBz$_3$

A solution containing 2.13 g (2.63 mmol) of Pd(DBA)$_3$ and 1.74 g (5.72 mmol, 10% excess) of PBz$_3$ in 150 ml of toluene was stirred for 2h 30 min at ambient temperature and was then evaporated to dryness. The solid thus obtained was washed with 100 ml and then twice with 20 ml of ether, which made it possible to isolate 1.85 g (1.95 mmol, Y=74%) of a yellow product.

IR(nujol) ν (cm$^{-1}$): 1640 (C═O). $^1$H NMR (200 MHz, C$_6$D$_6$) δ (ppm): 5.01 (d, $^3J_{H-H}$=10 Hz, 1H, olefinic H); 5.66 (d, $^3J_{H-H}$=10 Hz, 1H, olefinic H); 6.74 (d, $^3J_{H-H}$=15 Hz, 1H, olefinic H); 7.87 (d, $^3J_{H-H}$=15 Hz, 1H, olefinic H); 2.81 (d, $^2J_{H-P}$=5 Hz, 12 H, CH$_2$Ph); 7.1–7.5 (m, 40H, aromatic H). $^{31}$P-[$^1$H]NMR (80 MHz, C$_6$D$_6$) δ (ppm): 11.9 (broad s).

EXAMPLE 7

Pd(PCy$_2$PH)$_2$(C$_6$H$_5$)Cl←Pd(DBA) (PCy$_2$Ph)$_2$ + C$_6$H$_5$Cl

An orange-colored solution of the complex Pd(DBA)(PCy$_2$PH)$_2$ in 30 ml of chlorobenzene heated to 80° C. for 30 min quickly turned pale yellow. After the evaporation of the solvent to dryness, the product formed save for DBA was analyzed by NMR.

$^1$H NMR (200 MHz, C$_6$D$_6$) δ (ppm): 1.1–2.7 (m, 44H,Cy); 6.9 (m, 3H, meta and para H of PdC$_6$H$_5$); 7.15–7.25 (m, 6H, meta and para H of P-C$_6$H$_5$); 7.53 (d, 2H, ortho H of PdC$_6$H$_5$); 7.7–7.8 (m, 4H, ortho H of P-C$_6$H$_5$). $^{31}$P-[$^1$H]NMR (80 MHz, C$_6$D$_6$) δ (ppm): 24.4 (s).

EXAMPLE 8

Pd(PBz$_3$)$_2$(C$_6$H$_5$)Cl←Pd(DBA) (PBz$_3$)$_2$ + C$_6$H$_5$Cl

A solution containing 500 mg of Pd(DBA)(PBz$_3$)$_2$ in 100 ml of chlorobenzene was heated to 80° C. for 3 hours and was then evaporated to dryness. The solid residue was washed with ether and dried under vacuum. A slightly greyish product was isolated.

$^1$H NMR (200 MHz, C$_6$D$_6$) δ (ppm): 3.25 (t, 12H, $^2J_{H-P}$+$^4J_{H-P}$=6Hz, CH$_2$-C$_6$H$_5$); 6.7–7.55 (m, 35H, aromatic H). $^{31}$P-[$^1$H]NMR (80 MHz, C$_6$D$_6$) δ (ppm): 12.5 (s).

EXAMPLE 9

Pd(PCy$_3$)$_2$(C$_6$H$_4$COOEt)Cl←Pd(DBA)(PCy$_3$)$_2$ + ClC$_6$H$_4$COOEt 10 ml of ClC$_6$H$_4$COOEt were added to a solution containing 380 mg (0.42 mmol) of Pd(DBA)(PCy$_3$)$_2$ in 30 ml of toluene. After 10 minutes of stirring at 80° C., the mixture had turned from red to yellow. After evaporation of the solvent, a white solid was precipitated with acetone and was then isolated by filtration. 210 mg of an air-stable complex (0.25 mmol, Y=59%) was isolated.

IR(nujol) ν (cm$^{-1}$): 1710 (C═O). $^1$H NMR (200 MHz, C$_6$D$_6$) δ (ppm): 1.14 (t, J=7Hz, 3H, CH$_3$); 4.26 (q, J=7Hz, 2H, CH$_2$CH$_3$); 1.1-2.45 (m, 66H, PCy3); 7.91 (d, J=8Hz, 2H, arom. H); 8.18 (d, J=8Hz, 2H, arom. H). $^{31}$P-[$^1$H]NMR (80 MHz, C$_6$D$_6$) δ (ppm) : 23.1 (s).

EXAMPLE 10

Pd(PCy$_3$)$_2$(C$_6$H$_4$OCH$_3$)Cl←Pd(DBA)(PCy$_3$)$_2$ + ClC$_6$H$_4$OCH$_3$

The synthesis was performed under the same conditions as in Example 9. A reaction time of one hour was needed, however, to obtain quantitatively an airstable white product.

$^1$H NMR (200 MHz, C$_6$D$_6$) δ (ppm): 1.1–2.45 (m, 66H, PCy3); 3.58 (s, 3H, OCH3); 6.90 (d, J=8Hz, 2H, arom. H); 7.57 (d, J=8Hz, 2H, arom. H). $^{31}$P-[$^1$H]NMR (80 MHz, C$_6$D$_6$) δ (ppm): 23.1 (s).

EXAMPLE 11

Pd(PCy$_3$)$_2$(C$_6$H$_4$NO$_2$)Cl←Pd(DBA)(PCy$_3$)$_2$ + ClC$_6$H$_4$NO$_2$

A solution containing 500 mg (0.55 mmol) of Pd(DBA)(PCy$_3$)$_2$ and 1 g (6.35 mmol) of ClC$_6$H$_4$NO$_2$ in 50 ml of toluene was heated for 1 hour to 80° C. After evaporation of the solvent, the solid was washed with acetone, which resulted in 420 mg of a white product (0.51 mmol, Y=93%).

$^1$H NMR (200 MHz, C$_6$D$_6$) δ (ppm): 0.9–2.3 (m, 66H, PCy3); 7.70 (d, J=8Hz, 2H, arom. H); 8.03 (d, J=8Hz, 2H, arom. H). $^{31}$P-[$^1$H]NMR (80 MHz, C$_6$D$_6$) δ (ppm) : 23.4 (s).

What is claimed is:

1. A complex of the formula (I)

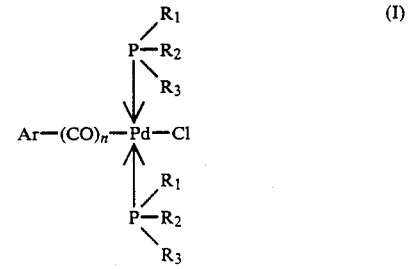

in which

Ar is a substituted or an unsubstituted mono- or polycyclic or heterocyclic aromatic radical each of R$_1$, R$_2$, and R$_3$ is identical or different and is selected from cyclohexyl, benzyl and isopropyl radicals, with the proviso that one of R$_1$, R$_2$, or R$_3$ can be a phenyl group when the other two are a cyclohexyl group, and n is an integer equal to 0 or 1.

2. A process for the preparation of the complex of formula (I)

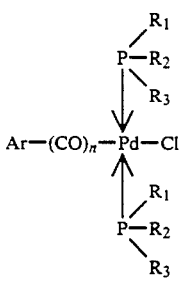

in which
Ar is a substituted or an unsubstituted mono- or polycyclic or heterocyclic aromatic radical
each of $R_1$, $R_2$, and $R_3$ is identical or different and is selected from cyclohexyl, benzyl and isopropyl radicals, with the proviso that one of $R_1$, $R_2$, or $R_3$ can be a phenyl group when the other two are a cyclohexyl group, and
n is an integer equal to 0 or 1,
which comprises bringing into contact a complex of the formula II

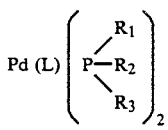

in which
$R_1$, $R_2$, and $R_3$ have the same meaning as in formula (I), and
L is a labile group, with a chloroaromatic compound of the formula ArCl, in which Ar has the same meaning as in formula (I).

3. A process as claimed in claim 2 in which n in formula (I) is equal to 1 which comprises bringing into contact said complex of formula II and said chloroaromatic compound with carbon monoxide.

4. The process as claimed in claim 2, wherein the labile group (L) is selected from dibenzylideneacetone and alkylene groups.

5. The process as claimed in claim 4, wherein the labile group (L) is ethylene.

6. A process for the preparation of the complex of formula (I),

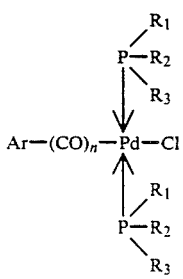

in which
Ar is a substituted or an unsubstituted mono- or polycyclic or heterocyclic aromatic radical,
each of $R_1$, $R_2$, and $R_3$ is identical or different and is selected from cyclohexyl, benzyl and isopropyl radicals, with the proviso that one of $R_1$, $R_2$, or $R_3$ can be a phenyl group when the other two are a cyclohexyl group, and
n is an integer equal to 0 or 1,
which comprises bringing into contact a palladium-diphosphine complex of the formula

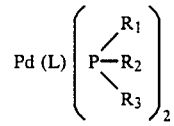

wherein $R_1$, $R_2$, and $R_3$ have the same meaning as in formula I or a complex of palladium and a labile group (L) of the formula Pd(L)$_3$ with a chlorinated aromatic compound of formula ArCl, wherein Ar has the same meaning as in said formula (I).

7. A process as claimed in claim 6 in which n in said formula (I) is equal to 1 which comprises bringing into contact said palladium-diphosphine complex or said complex of palladium and said labile group (L) with said chlorinated aromatic compound with carbon monoxide.

8. The process as claimed in claim 6, wherein the labile group (L) is selected from dibenzylideneacetone and alkylene groups.

9. The process as claimed in claim 8, wherein the labile group (L) is ethylene.

10. The process as claimed in claim 6 which comprises bringing phosphine into contact with said palladium M complex wherein the ratio of the number of moles of phosphine to the number of gram-atoms of palladium is from 2:1 to 5:1.

11. A process for the preparation of the complex of formula (I),

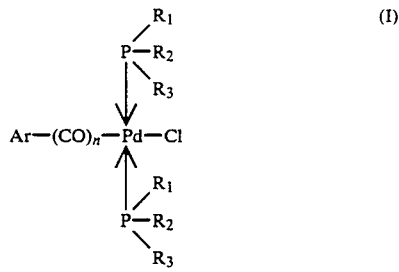

in which
Ar is substituted or an unsubstituted mono- or polycyclic or heterocyclic aromatic radical,
each of $R_1$, $R_2$, and $R_3$ is identical or different and is selected from cyclohexyl, benzyl and isopropyl radicals, with the proviso that one of $R_1$, $R_2$, or $R_3$ can be a phenyl group when the other two are a cyclohexyl group, and
n is an integer equal to 0 or 1,
which comprises bringing into contact a palladium (II) salt and at least two equivalents of a phosphine of the formula

wherein $R_1$, $R_2$, and $R_3$ have the same meaning as in said formula I.

12. A process as claimed in claim 11 in which n in said formula (I) is equal to 1 which comprises bringing into contact said palladium (II) salt and s id at least two equivalents of a phosphine with said chloroaromatic compound in the presence of a reducing agent with carbon monoxide.

13. The process as claimed in claim 11 which comprises bringing phosphine into contact with said palladium (II), wherein the ratio of the number of moles of phosphine to the number of gram-atoms of palladium is from 2:1 to 5:1.

14. A complex of the formula III

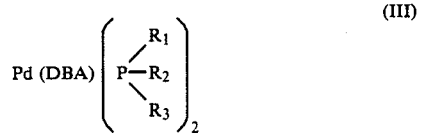

in which
DBA is dibenzylideneacetone
each of $R_1$, $R_2$, and $R_3$ is identical or different and is selected from cyclohexyl, isopropyl, benzyl and phenyl groups, with the proviso that only one of $R_1$, $R_2$, or $R_3$ is a phenyl group.

15. A process for the preparation of a complex of formula (III)

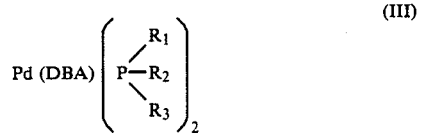

in which
each of $R_1$, $R_2$, and $R_3$ is identical or different and is selected from cyclohexyl, benzyl and isopropyl radicals, with the proviso that one of $R_1$, $R_2$, or $R_3$ can be a phenyl group when the other two are a cyclohexyl group, and which comprises bringing into contact in an organic solvent a dibenzylideneacetone (DBA) palladium complex salt of the formula Pd(PDA)$_3$ with at least two molar equivalents of a phosphine of the formula

wherein $R_1$, $R_2$, and $R_3$ have the same meaning as in formula (I).

* * * * *

UNITED STATES PATENT AND TRADEMARK OFFICE
CERTIFICATE OF CORRECTION

PATENT NO.   : 4,945,174
DATED        : July 31, 1990
INVENTOR(S)  : Marc Huser et al It is certified that error appears in the above-identified patent and that said Letters Patent is hereby corrected as shown below:

Claim 12, column 9, line 6, change "s id" to --said--.

Signed and Sealed this

Sixteenth Day of June, 1992

Attest:

DOUGLAS B. COMER

*Attesting Officer*   *Acting Commissioner of Patents and Trademarks*